US00PP31245P2

(12) United States Plant Patent
Chen et al.

(10) Patent No.: US PP31,245 P2
(45) Date of Patent: Dec. 17, 2019

(54) ***NELUMBO* PLANT NAMED 'BUZENG JIELU'**

(50) Latin Name: *Nelumbo nucifera*
Varietal Denomination: Buzeng Jielu

(71) Applicants: Yuchu Chen, Hangzhou (CN); Xun Zhao, Hangzhou (CN)

(72) Inventors: Yuchu Chen, Hangzhou (CN); Xun Zhao, Hangzhou (CN)

(73) Assignee: Zhejang Renwen Landscape Architecture Co., Ltd., Hangzhou (CN)

( * ) Notice: Subject to any disclaimer, the term of this patent is extended or adjusted under 35 U.S.C. 154(b) by 0 days.

(21) Appl. No.: 16/350,033

(22) Filed: Sep. 17, 2018

(51) Int. Cl.
*A01H 5/02* (2018.01)

(52) U.S. Cl.
USPC ..... Plt./342

(58) Field of Classification Search
USPC ..... Plt./342
CPC ..... A01H 6/00; A01H 5/00; A01H 5/02
See application file for complete search history.

*Primary Examiner* — Keith O. Robinson
(74) *Attorney, Agent, or Firm* — C. A. Whealy

(57) ABSTRACT

A new and distinct cultivar of *Nelumbo* plant named 'Buzeng Jielu', characterized by its upright plant habit; moderately vigorous growth habit; large medium green-colored leaves; freely flowering habit; and large red purple-colored calathiform flowers that are positioned above the foliar plane on moderately strong and erect peduncles.

2 Drawing Sheets

Botanical designation: *Nelumbo nucifera.*
Cultivar denomination: 'BUZENG JIELU'.

BACKGROUND OF THE INVENTION

The present invention relates to a new and distinct cultivar of *Nelumbo* plant, botanically known as *Nelumbo nucifera*, commonly referred to as Sacred or Indian Lotus, and hereinafter referred to by the name 'Buzeng Jielu'.

The new *Nelumbo* plant is a product of a controlled breeding program conducted by the Inventors in Hangzhou, Zhejiang, China. The objective of the breeding program is to create new *Nelumbo* plants that have attractive and unique flower forms and flower colors.

The new *Nelumbo* plant originated from an open-pollination in July, 2014 of *Nelumbo nucifera* 'Ziqi Xilai', not patented, as the female, or seed, parent with an unknown selection of *Nelumbo nucifera* as the male, or pollen, parent. The new *Nelumbo* plant was discovered and selected by the Inventors as a single flowering plant within the progeny of the stated open-pollination in a controlled greenhouse environment in Hangzhou, Zhejiang, China in July, 2016.

Asexual reproduction of the new *Nelumbo* plant by rhizome divisions in a controlled environment in Hangzhou, Zhejiang, China since April, 2017 has shown that the unique features of this new *Nelumbo* plant are stable and reproduced true to type in successive generations of asexual reproduction.

SUMMARY OF THE INVENTION

Plants of the new *Nelumbo* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Buzeng Jielu'. These characteristics in combination distinguish 'Buzeng Jielu' as a new and distinct *Nelumbo* plant:

1. Upright plant habit.
2. Moderately vigorous growth habit.
3. Large medium green-colored leaves.
4. Freely flowering habit.
5. Large red purple-colored calathiform flowers that are positioned above the foliar plane on moderately strong and erect peduncles.

Plants of the new *Nelumbo* differ from plants of the female parent, 'Ziqi Xilai', in the following characteristics:

1. Flowers of plants of the new *Nelumbo* are calathiform whereas flowers of plants of 'Ziqi Xilai' are more bowl-shaped.
2. Flowers of plants of the new *Nelumbo* have fewer petals and petaloids than flowers of plants of 'Ziqi Xilai'.

Plants of the new *Nelumbo* can be compared to plants of *Nelumbo nucifera* 'Xin Duo Mu', not patented. In side-by-side comparisons plants of the new *Nelumbo* differ primarily from plants of 'Xin Duo Mu' in flower shape as flowers of plants of the new *Nelumbo* are calathiform whereas flowers of plants of 'Xin Duo Mu' are more bowl-shaped.

Plants of the new *Nelumbo* can also be compared to plants of *Nelumbo nucifera* 'Zhu Luo Hong Yan', not patented. In side-by-side comparisons plants of the new *Nelumbo* differ primarily from plants of 'Zhu Luo Hong Yan' in flower shape as flowers of plants of the new *Nelumbo* are calathiform whereas flowers of plants of 'Zhu Luo Hong Yan' are plate-shaped.

BRIEF DESCRIPTION OF THE PHOTOGRAPHS

The accompanying photographs illustrate the overall appearance of the new *Nelumbo* plant showing the colors as true as it is reasonably possible to obtain in colored reproductions of this type. Colors in the photographs may differ slightly from the color values cited in the detailed botanical description which accurately describe the colors of the new *Nelumbo* plant.

The photograph on the first sheet is a side perspective view of a typical plant of 'Buzeng Jielu' grown in a container.

The photograph on the second sheet is a close-up view of a typical flower of 'Buzeng Jielu'.

DETAILED BOTANICAL DESCRIPTION

The aforementioned photographs and following observations and measurements describe plants grown during the summer in 37-cm by 35-cm containers in an outdoor nursery in Hangzhou, Zhejiang, China and under cultural practices typical of commercial *Nelumbo* production. During the production of the plants, day temperatures ranged from 14° C. to 33° C. and night temperatures ranged from 16° C. to 28° C. Plants were one year old when the photographs and the detailed description were taken. In the following description, color references are made to The Royal Horticultural Society Colour Chart, 2007 Edition, except where general terms of ordinary dictionary significance are used.

Botanical classification: *Nelumbo nucifera* 'Buzeng Jielu'.

Parentage:

*Female, or seed, parent.*—*Nelumbo nucifera* 'Ziqi Xilai', not patented.

*Male, or pollen, parent.*—Unknown selection of *Nelumbo nucifera*, not patented.

Propagation:

*Type.*—By rhizome divisions.

*Time to initiate roots, summer.*—About three to four days at temperatures about 27° C.

*Time to produce a rooted young plant.*—About seven days at temperatures about 27° C.

*Root description.*—Fine, fleshy; typically white to grey brown in color, actual color of the roots is dependent on water quality, fertilizer type and formulation, substrate temperature and physiological age of roots.

*Rooting habit.*—Not freely branching, medium density.

Plant Description:

*Plant and growth habit.*—Upright plant habit; moderately vigorous growth habit and moderate growth rate.

*Plant height (soil level to top of foliar plane).*—About 52 cm.

*Plant height (soil level to top of floral plane).*—About 76 cm.

*Plant diameter.*—About 140 cm by 110 cm.

Rhizome description:

*Arrangement and habit.*—Sympodial branching habit with about 11 to 16 primary branches developing per plant each with about 7.8 secondary branches.

*Length.*—About 70 cm to 210 cm.

*Diameter.*—About 1.2 cm to 4.2 cm.

*Internode length.*—About 11 cm to 42 cm.

*Texture and luster.*—Smooth, glabrous; glossy.

*Color.*—Close to 165C.

Leaf description:

*Length, fully expanded.*—About 18.5 cm to 29 cm.

*Width, fully expanded.*—About 15 cm to 25 cm.

*Shape.*—Peltate, elliptical.

*Apex.*—Retuse.

*Base.*—Cuneate.

*Margin.*—Entire; undulate.

*Venation.*—Palmate.

*Texture and luster, upper and lower surfaces.*—Pubescent, papery; slightly glossy.

*Color.*—Developing leaves, upper surface: Close to 144A. Developing leaves, lower surface: Close to 138B. Fully expanded leaves, upper surface: Close to 137B; venation, close to 137D. Fully expanded leaves, lower surface: Close to N138D; venation, close to 138B.

*Petioles.*—Length: About 41 cm. Diameter: About 5 mm to 7 mm. Strength: Moderately strong. Texture and luster, upper and lower surfaces: Smooth, glabrous; slightly glossy. Color: Close to 145A.

Inflorescence description:

*Arrangement.*—Double-type calathiform flowers developing directly from the rhizomes with numerous showy petals and petaloids; about 16 flower buds and flowers developing per plant at one time.

*Time to flower.*—In China, plants flower from June to August; flowering continuous during this period; flowers begin opening at 05:00 hours in the morning, flowers are fully opened at about 06:30 hours and are typically closed by 09:00 hours.

*Flower longevity.*—Flowers last about four to five days on the plant; flowers last about three days as a cut flower; flowers persistent; plants maintain good substance for about 45 days.

*Fragrance.*—Initially, very faint and then not detectable.

*Flower buds.*—Length: About 6.5 cm. Diameter: About 3.2 cm. Shape: Broadly ovate. Texture and luster: Smooth, glabrous; matte. Color: Close to 73A.

*Flowers.*—Shape and arrangement: Double-type, calathiform with numerous showy petals and petaloids. Diameter: About 15 cm. Height: About 10 cm.

*Petals.*—Quantity and arrangement: About 160 arranged in numerous whorls. Length: About 8.5 cm. Width: About 4.9 cm. Shape: Obovate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Close to 58A fading towards the base to close to 63C; at the base, close to 3D; venation, close to 58D; color becoming closer to 63D with development. When opening and fully opened, lower surface: Close to 58A fading towards the base to close to 63C; at the base, close to 3D; venation, close to 58D; color becoming closer to 63D with development.

*Petaloids.*—Quantity and arrangement: About 121 arranged in numerous whorls. Length: About 5.7 cm. Width: About 1.1 cm. Shape: Lanceolate. Apex: Acuminate. Base: Cuneate. Margins: Entire; not undulate. Texture and luster, upper surface: Slightly rugose, glabrous; slightly glossy. Texture and luster, lower surface: Smooth, glabrous; slightly glossy. Color: When opening and fully opened, upper surface: Close to 58A fading towards the base to close to 63C; at the base, close to 3D; venation, close to 58D; color becoming closer to 63D with development. When opening and fully opened, lower surface: Close to 58A fading towards the base to close to 63C; at the base, close to 3D; venation, close to 58D; color becoming closer to 63D with development.

*Sepals*.—Quantity and arrangement: About six in a single whorl. Length: About 6.7 cm. Width: About 5.1 cm. Shape: Obovate. Apex: Acuminate. Base: Cuneate. Texture and luster, upper and lower surfaces: Smooth, glabrous; matte. Color: When opening and fully opened, upper surface: Close to 63D. When opening and fully opened, lower surface: Close to 63C.

*Peduncles*.—Length: About 62 cm. Diameter: About 1.9 cm. Strength: Moderately strong. Aspect: Mostly erect. Texture and luster: Smooth, glabrous; slightly glossy. Color: Close to 145C.

*Stamens*.—Quantity per flower: About eight. Filament length: About 1.7 cm. Filament color: Close to 4C. Anther length: About 1.2 cm. Anther width: About 7 mm. Anther shape: Lanceolate. Anther color: Close to 6C. Pollen amount: Moderate. Pollen color: Close to 6C.

*Pistils*.—Quantity per flower: About 13. Pistil length: About 4.6 cm. Style length: About 2.5 cm. Style color: Close to 6A. Stigma diameter: About 1 mm. Stigma shape: Rounded. Stigma color: Close to 7A. Ovary color: Close to 6A.

*Fruits*.—Quantity per plant: About 18. Length: About 4.3 cm. Diameter: About 7.8 cm. Texture: Smooth, glabrous. Color: Close to 138A.

*Seeds*.—Quantity per fruit: About seven. Length: About 3.3 cm. Diameter: About 2.3 cm. Texture: Smooth, glabrous. Color: Close to N200B.

Pathogen & pest resistance: To date, plants of the new *Nelumbo* have not been observed to be resistant to pathogens or pests common to *Nelumbo* plants.

Temperature tolerance: Plants of the new *Nelumbo* have been observed to be tolerant to temperatures ranging from about −5° C. to about 42° C.

It is claimed:

1. A new and distinct *Nelumbo* plant named 'Buzeng Jielu' as illustrated and described.

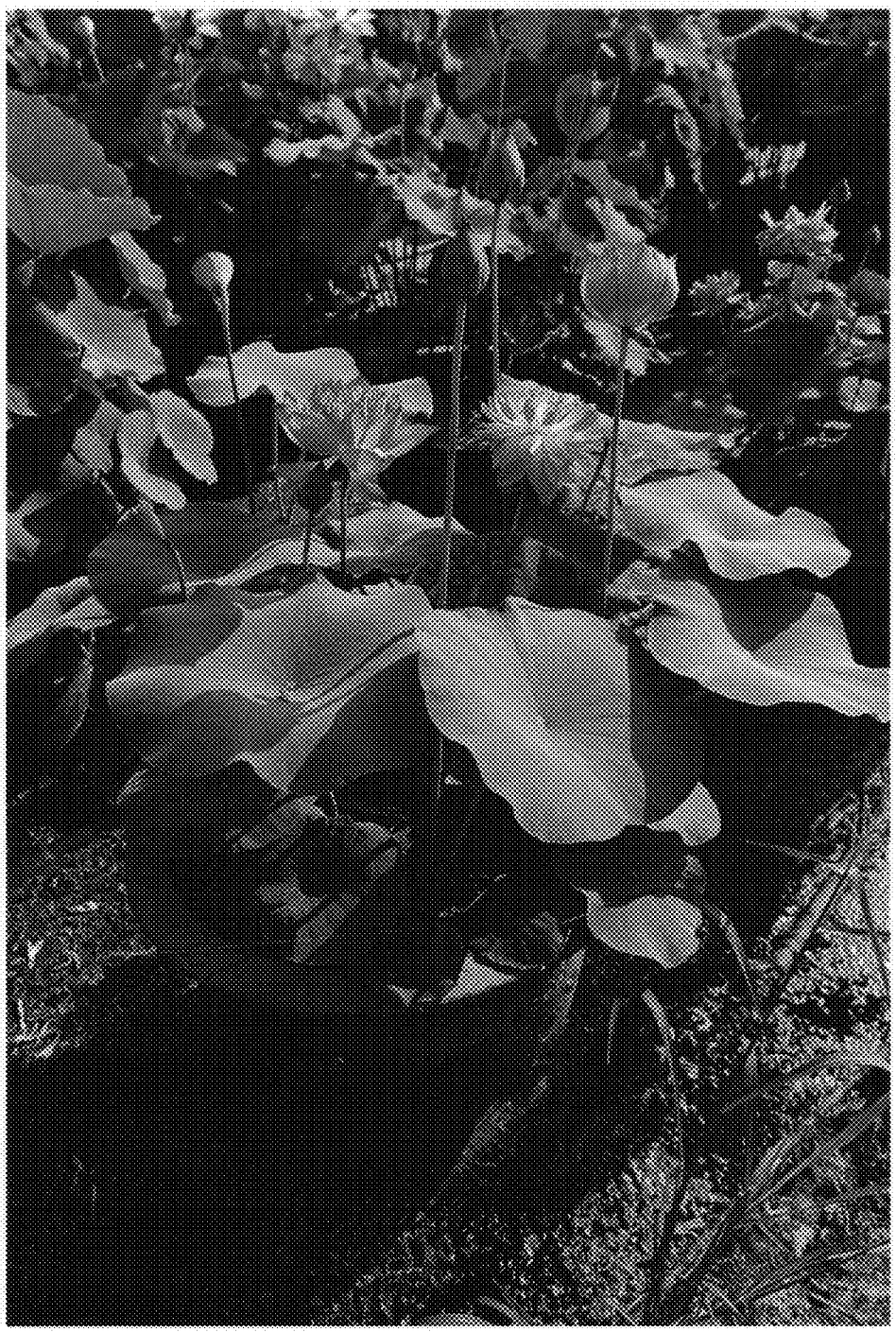

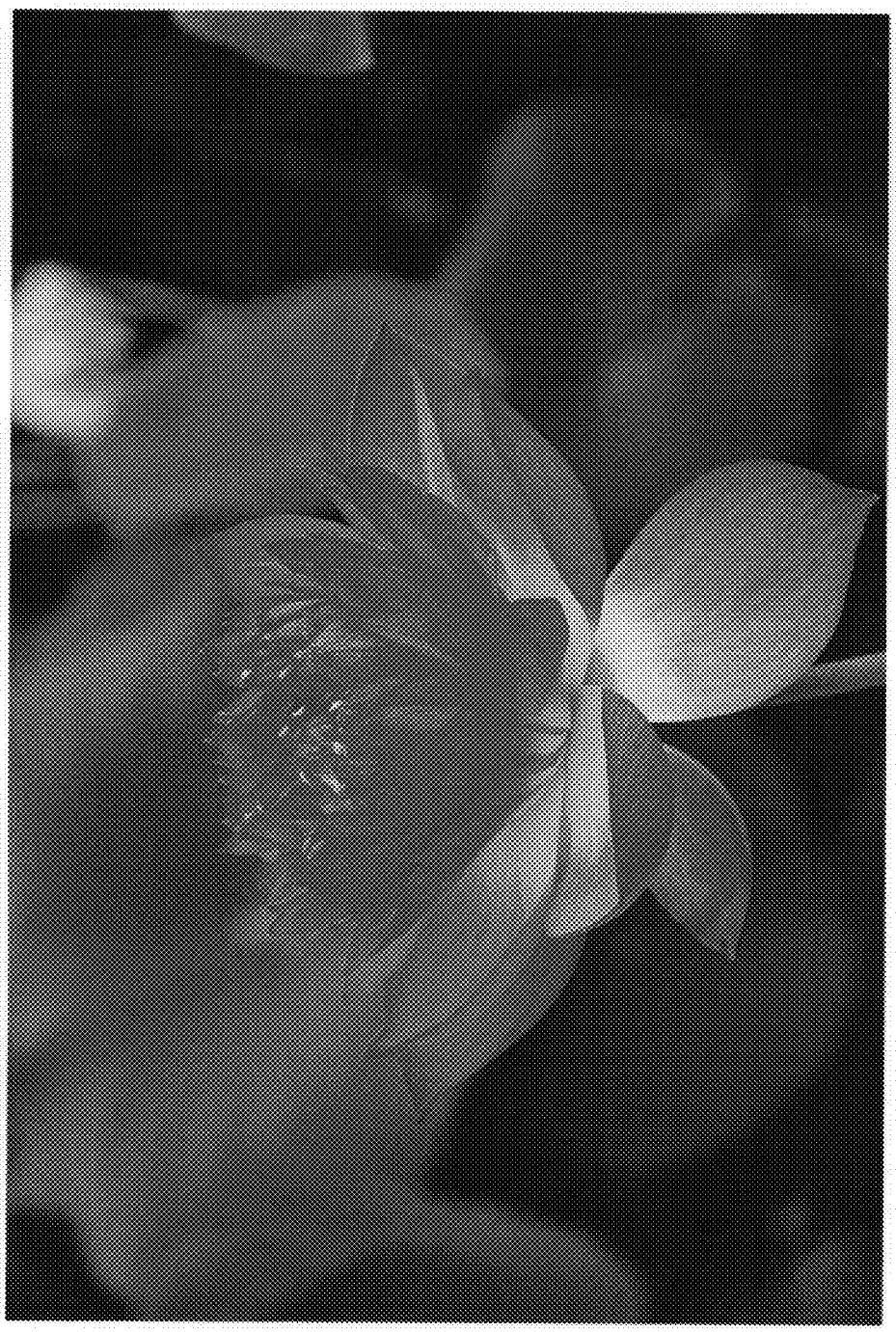

* * * * *